United States Patent [19]

Stroech et al.

[11] Patent Number: 4,954,162
[45] Date of Patent: Sep. 4, 1990

[54] AZOLYMETHYL-CYCLOPROPYL CARBINOL DERIVATIVES

[75] Inventors: Klaus Stroech, Solingen; Dietmar Beilefeldt, Ratingen; Wilhelm Brandes, Leichlingen; Stefan Dutzmann, Duesseldorf, all of Fed. Rep. of Germany

[73] Assignee: Bayer Aktiengesellschaft, Leverkusen, Fed. Rep. of Germany

[21] Appl. No.: 204,470

[22] Filed: Jun. 9, 1988

[30] Foreign Application Priority Data

Jun. 24, 1987 [DE] Fed. Rep. of Germany ....... 3720756

[51] Int. Cl.$^5$ ................. A01N 43/653; C07D 249/08
[52] U.S. Cl. .......................................... 71/92; 71/76; 514/184; 514/383; 548/101; 548/267.8; 548/262.6
[58] Field of Search ................ 514/184, 383; 548/101, 548/262; 71/92, 96

[56] References Cited

U.S. PATENT DOCUMENTS 4,715,887 12/1987 Kramer et al. .................. 71/92

FOREIGN PATENT DOCUMENTS 0086173  8/1983 European Pat. Off.
237917   9/1987 European Pat. Off. ............ 548/262
3617190 11/1986 Fed. Rep. of Germany .
0180136  5/1986 United Kingdom .

*Primary Examiner*—Glennon H. Hollrah
*Assistant Examiner*—Patricia L. Morris
*Attorney, Agent, or Firm*—Sprung Horn Kramer & Woods

[57] ABSTRACT

Fungicidal and plant-growth regulating azolymethyl-cyclopropyl carbinol derivatives of the formula

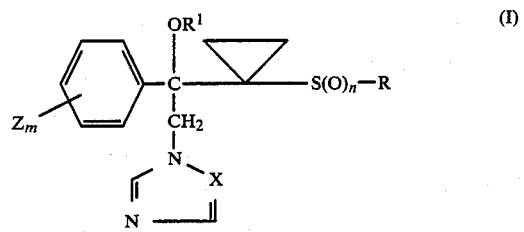

in which
R represents perfluroalkyl having 1 to 4 carbon atoms, trichloromethyl, difluorochloromethyl or fluorodichloromethyl,
$R^1$ represents hydrogen, alkl or acyl,
Z represents halogen, alkyl having 1 to 4 carbon atoms, alkoxy having 1 to 4 carbon atoms, alkylthio having 1 to 4 carbon atoms, halogenoakyl having 1 or 2 carbon atoms and 1 to 5 halogen atoms, halogenoalkoxy having 1 or 2 carbon atoms and 1 to 5 halogen atoms, halogenoalkythio having 1 to 2 carbon atoms and 1 to 5 halogen atoms, phenyl which is optionally substituted by alkyl having 1 to 2 carbon atoms and/or halogen, or phenoxy which is optionally substituted by alkyl having 1 or 2 carbon atoms and/or halogen,
m represents the numbers 0, 1, 2 or 3 and
n represents the numbers 0, 1 or 2 and
X represents nitrogen or a CH group, and addition products thereof with acids and metal salts.

12 Claims, No Drawings

AZOLYMETHYL-CYCLOPROPYL CARBINOL DERIVATIVES

The present invention relates to new azolylmethylcyclopropyl carbinol derivatives, several processes for their preparation and their use as fungicides and plant growth regulators.

It has already been disclosed that certain azolylmethyl-cyclopropyl carbinol derivatives possess fungicidal and plant growth regulatory properties (compare EP-OS (European Published Specification) No. 0,180,136 and DE-OS (German Published Specification) No. 3,617,190). Thus, for example, 1-(4-chlorophenyl)-1-[1-(methylthio)-1-cyclopropyl]-2-(1,2,4-triazol-1-yl)ethan-1-ol can be employed for combating fungi and for regulating plant growth. The activity of this substance is good; however, in some cases it leaves something to be desired at low application rates.

New azolylmethyl-cyclopropyl carbinol derivatives of the formula

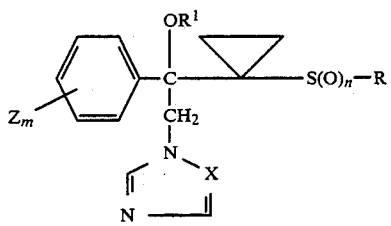

(I)

in which
R represents perfluoroalkyl having 1 to 4 carbon atoms, trichloromethyl, difluorochloromethyl or fluorodichloromethyl,
represents hydrogen, alkyl or acyl,
$R^1$ represents hydrogen, alkyl or acyl,
Z represents halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 halogen atoms, halogenoalkoxy having 1 or 2 carbon atoms and 1 to 5 halogen atoms, halogenoalkylthio having 1 or 2 carbon atoms and 1 to 5 halogen atoms, phenyl which is optionally substituted by alkyl having 1 or 2 carbon atoms and/or halogen, or phenoxy which is optionally substituted by alkyl having 1 or 2 carbon atoms and/or halogen,
m represents the numbers 0, 1, 2 or 3 and
n represents the numbers 0, 1 or 2 and
X represents nitrogen or a CH group, and also their acid addition salts and metal salt complexes, have now been found.

Furthermore, it has been found that azolylmethylcyclopropyl carbinol derivatives of the formula (I) and also their acid addition salts and metal salt complexes are obtained when (a) in a first step, phenyl-cyclopropyl ketones of the formula

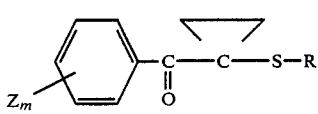

(II)

in which

R, Z and m have the abovementioned meaning, are reacted either (α) with dimethyloxosulphonium methylide of the formula

(III)

or (β) with dimethylsulphonium methylide of the formula

(IV)

in the presence of a diluent and
in a second step, the oxiranes of the formula

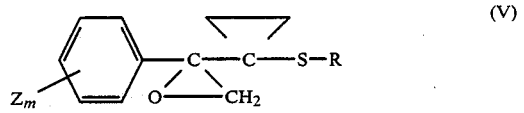

(V)

in which
R, Z and m have the abovementioned meaning, obtained in this reaction are reacted with azoles of the formula

(VI)

in which
X has the abovementioned meaning, in the presence of an acid-binding agent and in the presence of a diluent, or (b) azolylmethyl-cyclopropyl carbinol derivatives of the formula

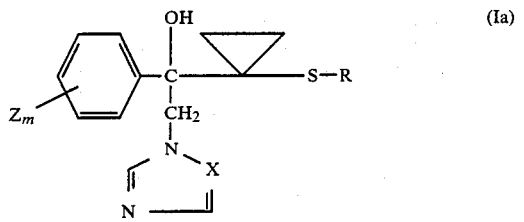

(Ia)

in which
R, X, Z and m have the abovementioned meaning, are reacted with oxidants, if appropriate in the presence of a diluent, or (c) azolylmethyl-cyclopropyl carbinol derivatives of the formula

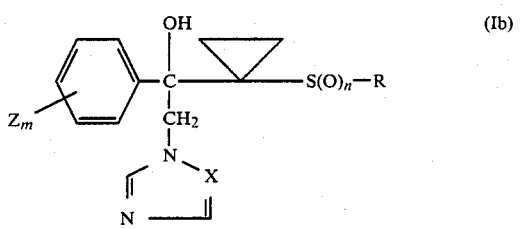

(Ib)

in which

R, Z, X, m and n have the abovementioned meaning, are reacted with strong bases in the presence of a diluent, and the alcoholates of the formula

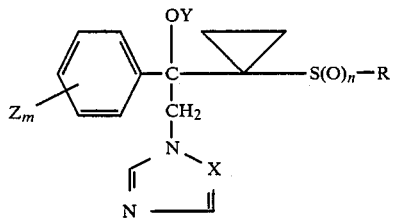 (Ic)

in which

R, X, Z, m and n have the abovementioned meaning and

Y represents a cationic radical of a base, produced in this reaction are reacted with halogen compounds of the formula $$R^2\text{-Hal} \quad \quad (VII)$$

in which $R^2$ represents alkyl or acyl and

Hal represents halogen, in the presence of a diluent, and if appropriate an acid or a metal salt is adducted to the compounds of the formula (I) thus obtained.

Finally, it has been found that the new azolylmethyl-cyclopropyl carbinol derivatives of the formula (I) and also their acid addition salts and metal salt complexes possess strong fungicidal and plant growth regulatory properties.

The substances according to the invention contain an asymmetrically substituted carbon atom. They can therefore occur in optical isomeric forms. The present invention relates both to the separate isomers and also to their mixtures.

Surprisingly, the substances according to the invention possess a better fungicidal and plant growth regulatory activity than 1-(4-chlorophenyl)-1-[1-(methylthio)-1-cyclopropyl]-2-(1,2,4-triazol-1-yl)-ethan-1-ol, which is constitutionally the most similar previously known active compound with an equivalent type of action.

Formula (I) provides a general definition of the azolylmethyl-cyclopropyl carbinol derivatives according to the invention. Preferably, in this formula R represents trifluoromethyl, trichloromethyl, difluorochloromethyl or fluorodichloromethyl, $R^1$ represents hydrogen, methyl, ethyl, n-propyl, isopropyl, n-butyl, isobutyl, methylcarbonyl, ethylcarbonyl, n-propylcarbonyl, isopropyl-carbonyl, n-butylcarbonyl and isobutyl-carbonyl, Z represents fluorine, chlorine, bromine, methyl, ethyl, isopropyl, tert.-butyl, methoxy, methylthio, trifluoromethyl, trifluoromethoxy, trifluoromethylthio, phenyl which is optionally substituted by fluorine, chlorine and/or methyl, or phenoxy which is optionally substituted by fluorine, chlorine and/or methyl, m represents the numbers 0, 1, 2 or 3, n represents the numbers 0, 1 or 2 and X represents nitrogen or a CH group.

When m represents the numbers 2 or 3, the radicals representing Z can be identical or different.

Addition products of acids and those azolylmethylcyclopropyl carbinol derivatives of the formula (I) in which R, $R^1$, X, Z, m and n have the meanings which have already been mentioned as preferable for these radicals and indices are also preferred compounds according to the invention.

The acids which can be adducted preferably include hydrohalic acids, such as, for example, hydrochloric acid and hydrobromic acid, in particular hydrochloric acid, and furthermore phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid and also sulphonic acids, such as, for example, p-toluenesulphonic acid, 1,5-naphthalenedisulphonic acid or camphorsulphonic acid.

Addition products of salts of metals of the main groups II to IV and the subgroups I and II and also IV to VIII of the periodic table of the elements and those azolylmethyl-cyclopropyl carbinol derivatives of the formula (I) in which R, $R^1$, X, Z, m and n have the meanings which have already been mentioned as preferable for these radicals and indices are additionally preferred compounds according to the invention. Salts of copper, zinc, manganese, magnesium, tin, iron and nickel are particularly preferred here. Possible anions of these salts are those which are derived from acids which lead to physiologically acceptable addition products. In this connection, particularly preferred acids of this type are the hydrohalic acids, such as, for example, hydrochloric acid and hydrobromic acid, and furthermore phosphoric acid, nitric acid and sulphuric acid.

The substances shown in the following table may be mentioned as examples of azolylmethyl-cyclopropyl carbinol derivatives of the formula (I).

TABLE (I)

| $Z_m$ | R | $R^1$ | X | n |
|---|---|---|---|---|
| 4-Cl | $CF_3$ | H | N | 0 |
| 2,4-$Cl_2$ | $CF_3$ | H | N | 0 |
| 2,4-$F_2$ | $CF_3$ | H | N | 0 |
| 4-Cl | $CF_3$ | H | CH | 0 |
| 4-Cl | $CF_3$ | H | CH | 1 |
| 4-Cl | $CF_3$ | H | CH | 2 |
| 4-Cl | $CF_3$ | $CH_3$ | N | 0 |
| 4-$CH_3$ | $CF_3$ | H | N | 0 |
| 4-$CF_3$ | $CF_3$ | H | N | 0 |
| 4-$OCF_3$ | $CF_3$ | H | N | 0 |
| 4-$SCF_3$ | $CF_3$ | H | N | 0 |
| 4-$OCH_3$ | $CF_3$ | H | N | 0 |
| 4-$SCH_3$ | $CF_3$ | H | N | 0 |
| 2,4,6-$Cl_3$ | $CF_3$ | H | N | 0 |
| 4-(phenyl) | $CF_3$ | H | N | 0 |
| 4-O-(phenyl) | $CF_3$ | H | N | 0 |
| 4-t-$C_4H_9$ | $CF_3$ | H | N | 0 |
| 2-Cl, 4-$CH_3$ | $CF_3$ | H | N | 0 |

TABLE-continued

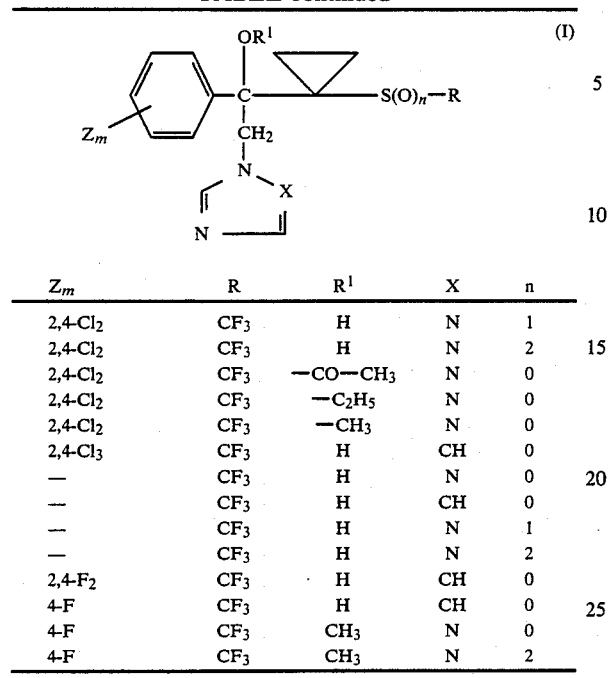

| $Z_m$ | R | $R^1$ | X | n |
|---|---|---|---|---|
| 2,4-Cl$_2$ | CF$_3$ | H | N | 1 |
| 2,4-Cl$_2$ | CF$_3$ | H | N | 2 |
| 2,4-Cl$_2$ | CF$_3$ | —CO—CH$_3$ | N | 0 |
| 2,4-Cl$_2$ | CF$_3$ | —C$_2$H$_5$ | N | 0 |
| 2,4-Cl$_2$ | CF$_3$ | —CH$_3$ | N | 0 |
| 2,4-Cl$_3$ | CF$_3$ | H | CH | 0 |
| — | CF$_3$ | H | N | 0 |
| — | CF$_3$ | H | CH | 0 |
| — | CF$_3$ | H | N | 1 |
| — | CF$_3$ | H | N | 2 |
| 2,4-F$_2$ | CF$_3$ | H | CH | 0 |
| 4-F | CF$_3$ | H | CH | 0 |
| 4-F | CF$_3$ | CH$_3$ | N | 0 |
| 4-F | CF$_3$ | CH$_3$ | N | 2 |

If 2,4-difluorophenyl-1-(trifluoromethylmercapto)-cycloprop-1-yl ketone and dimethyloxosulphonium methylide are used as starting materials and 1,2,4,-triazole as a reaction component, then the course of the process (a) according to the invention can be illustrated by the following equation:

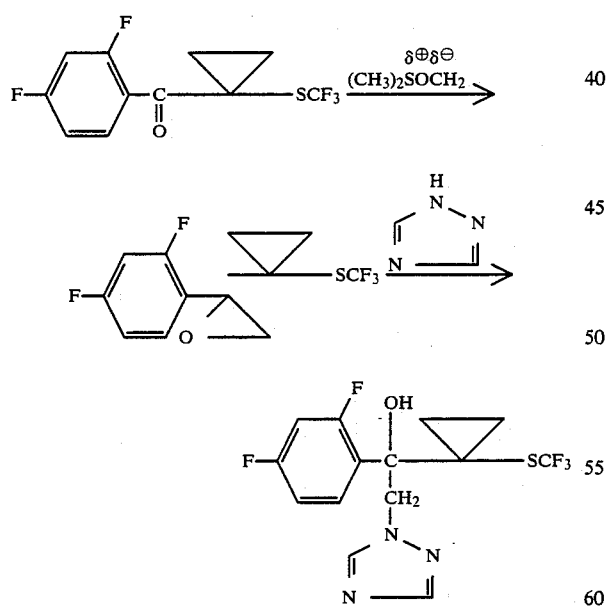

If 1-(2,4-difluorophenyl)-1-hydroxy-2-(1,2,4-triazol-1-yl)-1-(1-trifluoromethylmercapto-cycloprop-1-yl)ethane and hydrogen peroxide in glacial acetic acid are used as starting materials, then the course of the process (b) according to the invention can be illustrated by the following equation:

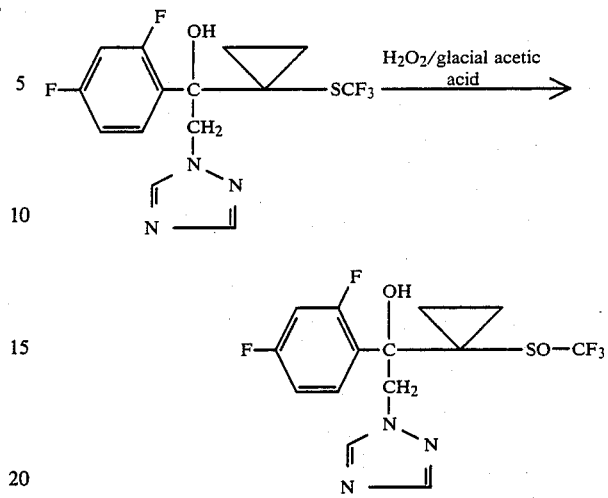

If 1-(2,4-difluorophenyl)-1-hydroxy-2-(1,2,4-triazol-1-yl)-1-(1-trifluoromethylmercapto-cycloprop-1-yl)ethane and sodium hydride are used as starting materials and iodomethane as the reaction component, then the course of the process (c) according to the invention can be illustrated by the following equation:

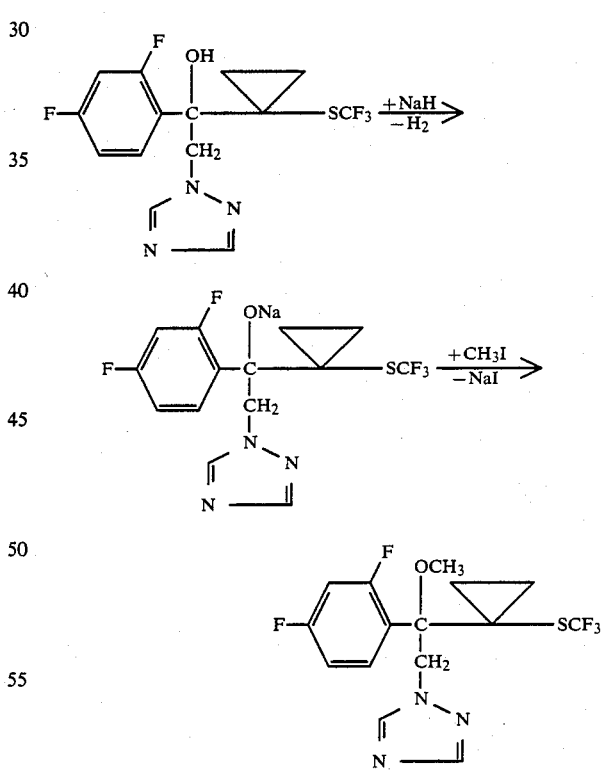

Formula (II) provides a general definition of the phenyl-cyclopropyl ketones required as starting materials in the process (a) according to the invention. In this formula, R, Z and m preferably have those meanings which have already been mentioned in connection with the description of the substances according to the invention, of the formula (I), as preferable for these radicals or this index.

The phenyl-cyclopropyl ketones of the formula (II) were hitherto unknown. They can be prepared by a process (d) in a first step, phenyl ketones of the formula

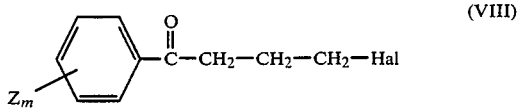

(VIII)

in which

Z and m have the abovementioned meaning and

Hal represents chlorine or bromine, are reacted with mercaptans of the-formula

 (IX)

in which

R has the abovementioned meaning and

Hal' represents chlorine or bromine, in the presence of a diluent, and the resulting phenylpropyl ketones of the formula

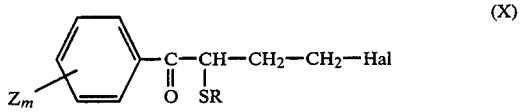

(X)

in which

R, Z, Hal and m have the abovementioned meaning, are reacted in a second step in the presence of an acid-binding agent and in the presence of a diluent.

The phenyl ketones of the formula (VIII) required as starting materials in process (d) are known or can be prepared in a simple manner by processes which are known in principle (compare DE-OS (German Published Specification) No. 2,521,104, DE-OS (German Published Specification) No. 2,320,355 and DE-OS (German Published Specification) No. 2,351,948). Thus phenyl ketones of the formula (VIII) are obtained by a process in which benzene derivatives of the formula

(XI)

in which and m have the abovementioned meaning, are reacted with butyric acid halides of the formula

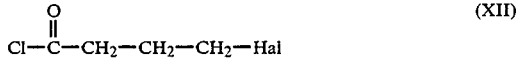

(XII)

in which

Hal has the abovementioned meaning, in the presence of a Friedel-Crafts catalyst, such as, for example, aluminum chloride, if appropriate in the presence of a diluent, such as, for example, methylene chloride, at temperatures between −15° C. and +60° C.

The mercaptans of the formula (IX) furthermore required as starting materials in the process (d) are known.

In carrying out the first step of the process (d), possible diluents are all inert organic solvents customary for such reactions. Halogenated aliphatic hydrocarbons, such as, for example, methylene chloride, chloroform and carbon tetrachloride, are preferably utilizable.

In carrying the first step of the process (d), the reaction temperatures can be varied within a certain range. In general, the reaction is carried out at temperatures between 0° C. and 80° C., preferably between 10 and 50° C.

In carrying out the first step of the process (d), 2 to 4 moles of mercaptans of the formula (IX) are generally employed per mole of phenyl ketone of the formula (VIII). The isolation of the resulting phenyl propyl ketones of the formula (X) is by customary methods. Generally, a procedure is used in which the solvent is stripped off and the remaining product is employed for further synthesis either directly or after previous purification.

In carrying out the second step of the process (d), possible acid-binding agents are all bases customary for such reactions. Alcoholates, such as sodium methylate or potassium tert.-butylate, and furthermore lower tertiary alkylamines, cycloalkylamines and aryl alkylamines, such as triethylamine, dimethyl-aniline, 1,5-diazabicyclo[4,3,0]non-5-ene and 1,8-diazabicyclo-[5,4,0]undecene, are preferably utilizable.

In carrying out the second step of process (d), suitable diluents are all inert organic solvents customary for such reactions. Alcohols, such as methanol, ethanol, methoxyethanol, propanol or tert.-butanol, and furthermore ketones, such as acetone and butan-2-one, and additionally nitriles, such as acetonitrile, and furthermore esters, such as ethyl acetate, and moreover ethers, such as dioxane, aromatic hydrocarbons, such as benzene or toluene, and also amides, such as dimethylformamide, are preferably utilizable.

In carrying out the second step of the process (d), the temperatures can also be varied within a relatively wide range Generally, the reaction is carried out at temperatures between 0° C. and 100° C., preferably between 20° C. and 60° C.

In carrying out the second step of the process (d), 1 to 3 moles of base are generally employed per mole of phenyl-propyl ketone of the formula (X). Working up is by customary methods. In general, a procedure is used in which the reaction mixture is mixed with water, then the mixture is extracted with an organic solvent which is sparingly soluble in water, and the combined organic phases are washed with water and concentrated after drying. The remaining product can be freed from impurities which may still be present by customary methods, such as, for example, column chromatography.

The dimethyl-oxo-sulphonium methylide of the formula (III) required as a reaction component in the process (a) according to the invention is known (compare J. Am. Chem. Soc. 87, 1363–1364 (1965)). It is used in the above reaction in the freshly prepared state, by producing it in situ by reaction of trimethyloxosulphonium iodide with sodium hydride or sodium amide, in particular with potassium tert.-butylate or sodium methylate, in the presence of a diluent.

The dimethylsulphonium methylide of the formula (IV) additionally possible as a reaction component in the process (a) according to the invention is likewise known (compare Heterocycles 8, 397 (1977)). It is likewise employed in the above reaction in the freshly prepared state, by producing it in situ, for example, from trimethylsulphonium halide or trimethylsulphonium methylsulphate, in the presence of a strong base, such as, for example, sodium hydride, sodium amide, sodium methylate, potassium tert.-butylate or potassium hydroxide, in the presence of a diluent, such as tert.-butanol or dimethyl sulphoxide.

The oxiranes of the formula (V) occurring as intermediates in the process (a) according to the invention were hitherto known. They represent generally important intermediates.

The azoles of the formula (VI) required as reaction components for the second step of the process (a) according to the invention are generally known compounds of organic chemistry.

Suitable diluents in carrying out the first step of the process (a) according to the invention are inert organic solvents. Alcohols, such as tert.-butanol, ethers, such as tetrahydrofuran or dioxane, and furthermore aliphatic and aromatic hydrocarbons, such as benzene, toluene or xylene, and also strongly polar solvents, such as dimethyl sulphoxide, are preferably utilizable.

In carrying out the first step of the process according to the invention, the reaction temperatures can be varied within a relatively wide range. Generally, the reaction is carried out between 0° C. and 100° C., preferably between 10° C. and 60° C.

In carrying out the first step of the process (a) according to the invention, 1 to 3 moles of dimethyloxosulphonium methylide of the formula (III) or dimethylsulphonium methylide of the formula (IV) are generally employed per mole of phenylcyclopropyl ketone of the formula (II). Isolation of the oxiranes of the formula (V) is by customary methods.

The second step of the process (a) according to the invention is carried out in the presence of a base. In this context, all conventionally utilizable inorganic and organic bases are possible. Alkali metal carbonates, such as, for example, sodium carbonate and potassium carbonate; alkali metal hydroxides, such as, for example, sodium hydroxide; alkali metal alcoholates, such as, for example, sodium methylate or potassium methylate and sodium ethylate or potassium ethylate; alkali metal hydrides, such as, for example, sodium hydride, and also lower tertiary alkylamines, cycloalkylamines and aralkylamines, such as triethylamine in particular, are preferably utilizable.

Suitable diluents for the second step of the process (a) according to the invention are inert organic solvents. Nitriles, such as acetonitrile in particular; aromatic hydrocarbons, such as benzene, toluene and dichlorobenzene; formamides, such as dimethylformamide in particular, and also hexamethylphosphoric triamide, are preferably utilizable.

In carrying out the second step of the process (a) according to the invention, the reaction temperatures can be varied within a relatively wide range. Generally, the reaction is carried out at temperatures between 0° C. and 200° C., preferably between 60° C. and 150° C.

In carrying out the second step of the process (a) according to the invention, 1 to 2 moles of azole of the formula (VI) and 1 to 2 moles of base are preferably employed per mole of oxirane of the formula (V). The final products are isolated in a conventional manner.

The azolylmethyl-cyclopropyl carbinol derivatives of the formula (Ia) required as starting materials for the process (b) according to the invention are compounds according to the invention.

Suitable reaction components in process (b) according to the invention are all oxidants customary for such reactions. Hydrogen peroxide and peracids, such as m-chloroperbenzoic acid and peracetic acid are preferably utilizable.

In carrying out process (b) according to the invention, about 1 to 5 moles of oxidant are employed per mole of compounds according to the invention of the formula (Ia). On use of 1 mole of oxidant, such as m-chloroperbenzoic acid in methylene chloride or hydrogen peroxide in acetic acid or acetic anhydride at temperatures between $-30°$ C. to $+90°$ C., the SO group-containing compounds of the formula (I) according to the invention preferentially result. With excess oxidant and temperatures between, 10° C. and 90° C,. the compounds according to the invention, of the formula (I), having the $-SO_2$ grouping preferably result. Isolation of the oxidation products is in a conventional manner.

The azolylmethyl-cyclopropyl carbinol derivatives of the formula (Ib) required as starting materials for the process (c) according to the invention are likewise compounds according to the invention. They are converted into the corresponding alcoholates in a generally known manner, by a procedure in which they are reacted with suitable strong bases, such as alkali metal amides or alkali metal hydrides, quaternary ammonium hydroxides or phosphonium hydroxides in an inert diluent, such as, for example, dioxane, at room temperature. Accordingly, in the compounds of the formula (Ic), Y preferably represents an alkali metal cation, such as a sodium or potassium cation, or a quaternary ammonium or phosphonium cation.

Formula (VII) provides a general definition of the halogen compounds additionally required as starting materials in the process (c) according to the invention. In this formula, $R^2$ preferably represents those meanings which have already been mentioned for the substituent $R^1$ in connection with the description of the substances, of the formula (I) according to the invention, excluding the meaning hydrogen. Hal preferably represents chlorine or bromine.

The halogen compounds of the formula (VII) are known or can be prepared by methods which are known in principle.

Suitable diluents in carrying out the process (c) according to the invention are inert organic solvents. These preferably include ethers, such as diethyl ether or dioxane; aromatic hydrocarbons, such as benzene; in individual cases also chlorinated hydrocarbons, such as chloroform, methylene chloride or carbon tetrachloride; and also hexamethylphosphoric triamide.

In carrying out the process (c) according to the invention, the reaction temperatures can be varied within a relatively wide range. Generally, the reaction is carried out at between 0° C. and 120° C., preferably between 20° C. and 100° C.

In carrying out the process (c) according to the invention, hydroxy compounds of the formula (Ib) are initially reacted with strong bases to give the corresponding alcoholates of the formula (Ic). In the following step, 1 to 2 moles of halogen compound of the formula (VII) are preferably employed per mole of alcoholate of the formula (Ic).

To isolate the final products, the reaction mixture is freed from solvent and water and an organic solvent are added to the residue. The organic phase is separated off, worked up in a conventional manner and purified.

In a preferred embodiment, it is expedient to proceed by commencing from a hydroxyl compound of the formula (Ib), to convert the latter using alkali metal hydride or alkali metal amide in a suitable organic solvent into the alkali metal alcoholate and to react the latter immediately without isolation with a halogen compound of the formula (VII), the compounds of the formula (I) according to the invention being obtained in one operation with the release of alkali metal halide.

According to a further preferred embodiment, the preparation of the alcohols and also the reaction with a halogen compound of the formula (VII) are expediently carried out in a two-phase system, such as, for example, aqueous sodium hydroxide solution or potassium hydroxide solution/toluene or methylene chloride, with the addition of 0.01-1 mole of a phase-transfer catalyst, such as, for example, ammonium or phosphonium compounds, the alcoholates being reacted in the organic phase or on the boundary with the halides present in the organic phase.

The azolylmethyl-cyclopropyl carbinol derivatives of the formula (I) obtainable by the process according to the invention can be converted into acid addition salts or metal salt complexes.

For the preparation of acid addition salts of the compounds of the formula (I), suitable acids are preferably those which have already been mentioned as preferred acids in connection with the description of the acid addition salts according to the invention.

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtering off, and purified, if appropriate by washing with an inert organic solvent.

For the preparation of metal salt complexes of the compounds of the formula (I), suitable salts of metals are preferably those which have already been mentioned as preferred metal salts in connection with the description of the metal salt complexes according to the invention.

The metal salt complexes of the compounds of the formula (I) can be obtained in a simple manner by customary processes, thus, for example, by dissolving the metal salt in alcohol, for example ethanol, and adding to compounds of the formula (I). Metal salt complexes can be isolated in a known manner, for example by filtering off, and purified, if appropriate by recrystallization.

The compounds according to the invention exhibit a strong microbicidal action and can be employed as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as *Xanthomonas oryzae*; Pseudomonas species, such as *Pseudomonas lachrymans*; Erwinia species, such as *Erwinia amylovora*; Pythium species, such as *Pythium ultimum*; Phytophthora species, such as *Phytophthora infestans*; Pseudoperonospora species, such as *Pseudo peronospora humuli* or *Pseudoperonospora cubense*; Plasmopara species, such as *Plasmopara viticola*; Peronospora species, such as *Peronospora pisi* or *P. brassicae*; Erysiphe species, such as *Erysiphe graminis*; Sphaerotheca species, such as *Sphaerotheca fuliginea*; Podosphaera species, such as *Podosphaera leucotricha*; Venturia species, such as Venturia inaequalis; Pyrenophora species, such as *Pyrenophora teres* or *P. graminea*; (conidia form: Drechslera, syn: Helminthosporium); Cochliobolus species, such as *Cochliobolus sativus*; (conidia form: Drechslera, syn: Helminthosporium); Uromyces species, such as *Uromyces appendiculatus*; Puccinia species, such as *Puccinia recondita*; Tilletia species, such as *Tilletia caries*; Ustilago species, such as *Ustilago nuda* or *Ustilago avenae*; Pellicularia species, such as *Pellicularia sasakii*; Pyricularia species, such as *Pyricularia oryzae*; Fusarium species, such as *Fusarium culmorum*; Botrytis species, such as *Botrytis cinerea*; Septoria species, such as *Septoria nodorum*; Leptosphaeria species, such as *Leptosphaeria nodorum*; Cercospora species, such as *Cercospora canescens*; Alternaria species, such as *Alternaria brassicae* and Pseudocercosporella species, such as *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating Venturia in fruit growing for combating Erysiphe, Lepto-sphaeria, Pseudocercosporella and Fusarium in the cultivation of cereals, and also for combating Pyricularia in rice. The substances according to the invention also show a broad in vitro action.

Moreover, the active compounds according to the invention also possess plant-growth regulatory properties.

The active compounds according to the invention engage in the metabolism of the plants and can therefore be employed as growth regulators.

Experience to date of the mode of action of plant growth regulators has shown that an active compound can also exert several different actions on plants. The actions of the substances depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating substances can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of bending ('lodging') of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beets, sugar cane, pineapples and citrus fruit or to increase the protein content in soy beans or cereals. Using growth regulators it is also possible, for example, to inhibit the degradation of desired constituents, such as, for example, sugar in sugar beets or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ('thinning out') in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolysis products; as dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants When the substances according to the invention are employed as fungicides, the amount applied can be varied within a relatively wide range, depending upon the type of application. Thus, in the treatment of parts of plants, the active compound concentrations in the use forms are, in general, between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02%, are required at the place of action.

When the compounds according to the invention are used as plant growth regulators, the amounts applied can be varied within a substantial range. In general, 0.01 to 50 kg, preferably 0.05 to 10 kg, of active compound are used per hectare of soil surface.

When the substances according to the invention are used as plant growth regulators, the rule is that application takes place within a preferred period of time, the exact definition of which depends on the climatic and vegetative circumstances.

The preparation and the use of the active compounds according to the invention can be seen from the examples below.

PREPARATION EXAMPLES

Example 1

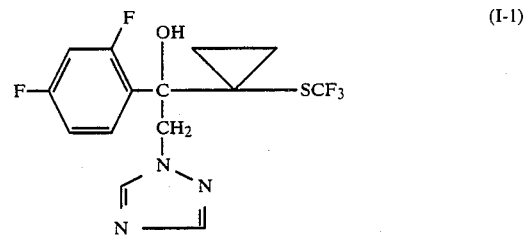

A solution of 15.9 g (54 mmol) of 2-(2,4-difluorophenyl)-2-[1-(trifluoromethylmercapto)-cycloprop-1-yl]oxirane in 20 ml of absolute dimethylformamide is added dropwise with stirring to a mixture of 12 g (174 mmol) of 1,2,4-triazole and 1.4 g (12.5 mmol) of potassium tert.butylate in 30 ml of absolute dimethylformamide under a nitrogen atmosphere The reaction mixture is stirred at 100° C. for 8 hours. The solvent is then stripped off under reduced pressure, the residue is taken up in ethyl acetate, and the solution is washed twice with water and concentrated under reduced pressure after drying over sodium sulphate The residue is chromatographed on a silica gel column using chloroform as eluent. In this manner, 12.5 g (65 % of theory) of 1-(2,4-difluorophenyl)-1-hydroxy-2-(1,2,4-triazol-1-yl)-1-(1-trifluoromethylmercapto-cycloprop-1-yl)ethane of melting point 103° C. are obtained.

Preparation of Starting Products

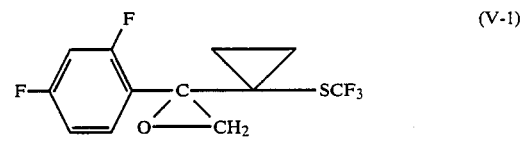

50 ml of absolute dimethyl sulphoxide are added dropwise to a mixture of 1.9 g (63 mmol) of sodium hydride (80 % strength) and 13.5 g (61 mmol) of trimethyloxosulphonium iodide at 10° C. under a nitrogen atmosphere. The mixture is stirred for a further hour at 10° C. and then a solution of 15.3 g (54 mmol) of 2,4-difluorophenyl-(1-trifluoromethylmercapto-cycloprop-1-yl)ketone in 20 ml of absolute dimethyl sulphoxide is added dropwise at the same temperature. The reaction mixture is stirred for 48 hours at room temperature and then for 1 hour at 40° C. and then poured into water. The mixture is extracted with ethyl acetate, and the combined organic phases are washed with water, dried over sodium sulphate and concentrated under reduced pressure. 15.9 g (99 % of theory) of 2-(2,4-difluorophenyl)-2-[1-(trifluoromethylmercapto)-cycloprop1-yl]oxirane are obtained in the form of a colorless oil.

$^1$H-NMR (360MHz; CDCl$_3$): $\delta$=1.00–1.50 (m, 4H); 3.04 (m, 2H); 6.80–6.96 (m, 2H); 7.38–7.48 (m, 1H).

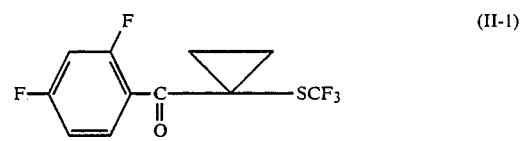

A solution of 47 g (0.15 mol) of (3-chloro-1-trifluoromethylmercapto-propyl)-(2,4-difluorophenyl)ketone in 70 ml of tert.-butanol is added dropwise at 40° C. with stirring to a mixture of 20 g (0.18 mol) of potassium tert.-butylate and 50 ml of tert.-butanol. The reaction mixture is stirred for 4 hours at 40° C. and then poured into water. The mixture is extracted with ethyl acetate, and the combined organic phases are washed with water, dried over sodium sulphate and concentrated by stripping off the solvent under reduced pressure. The residue remaining is chromatographed on a silica gel column with petroleum ether:methylene chloride=1:0.4 as eluent. 15.3 g (36% of theory) of 2,4-difluorophenyl-(1-trifluoromethylmercaptocycloprop-1-yl)ketone are obtained in the form of a colorless oil.

$^1$H-NMR (200 MHz, CDCl$_3$): δ=1.57 (m, 2H); 1.95 (m, 2H);
6.80–7.02 (m, 2H); 7.55–7.68 (m, 1H).

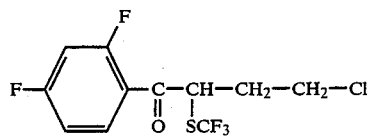

(X-1)

75 g (0.55 mol) of trifluoromethylsulphenyl chloride are added at 20 to 25° C. with stirring to a solution of 43 g (0.2 mol) of 3-chloropropyl-2,4-difluorophenyl ketone in 100 ml of methylene chloride. The mixture is stirred at room temperature for 108 hours and then concentrated by stripping off the solvent under reduced pressure. 63 g of (3-chloro-1-trifluoromethylmercapto-propyl)-2,4-difluorophenyl ketone are obtained.

$^{19}$F-NMR (external standard: CF$_3$COOH): δ= −36.6 ppm (doublet), +24.5 ppm (multiplet), +27.9 ppm (multiplet).

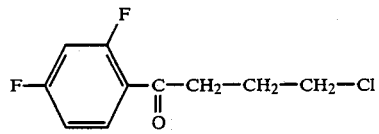

(VIII-1)

62 g (0.44 mol) of 4-chlorobutyric acid chloride are added dropwise at 20° C. with stirring to a mixture of 50 g (0.44 mol) of 1,3-difluorobenzene and 64 g (0.48 mol) of anhydrous aluminum chloride. The reaction mixture is stirred at 30° C. for 3.5 hours until a clear solution results and evolution of gas has ceased. After cooling to room temperature, 300 ml of methylene chloride are added. The resultant solution is poured onto 300 g of ice, and the organic phase is separated off, dried over sodium sulphate and concentrated by stripping off the solvent under reduced pressure. 83 g (86% of theory) of 3-chloropropyl2,4-difluorophenyl ketone are obtained in the form of a liquid. b.p. =80° C./0.1 mbar.

Example 2

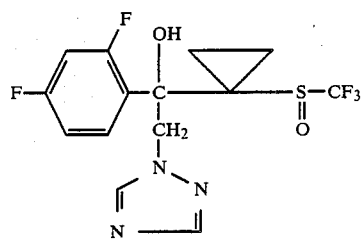

(I-2)

6 ml of 35% strength hydrogen peroxide solution are added dropwise with stirring to a solution of 4 g of 1-(2,4-difluorophenyl)-1-hydroxy-2-(1,2,4-triazol-1-yl)1-(1-trifluoromethylmercapto-cycloprop-1yl)ethane in 30 ml of glacial acetic acid at 85° C. The reaction mixture is stirred for 4 hours at 85° C. and then poured into 80 ml of water. The solution is rendered basic by the addition of dilute, aqueous sodium hydroxide solution. The solution is extracted repeatedly with methylene chloride, and the combined organic phases are washed with dilute, aqueous sodium hydroxide solution and water, then dried over sodium sulphate and concentrated by stripping off the solvent under reduced pressure. The residue remaining is purified by chromatography on silica gel. 1.7 g (41 % of theory) of 1-(2,4-difluorophenyl)-1-hydroxy-2-(1,2,4-triazol-1-yl)1-(trifluoromethylsulphoxy-cycloprop-1-yl)ethane of melting point 101° C. are obtained The compounds shown in the following examples were also prepared by the method given in Example 1:

Example 3

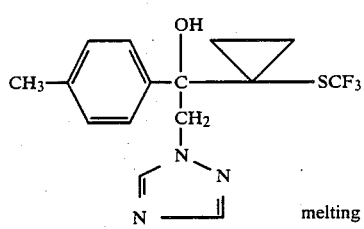

(I-3)

melting point 127° C.

Example 4 OH

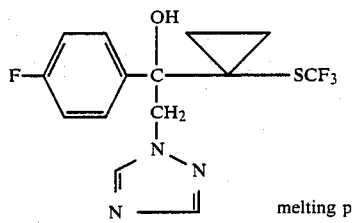

(I-4)

melting point 128° C.

Example 5

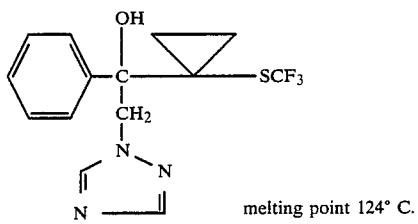

melting point 124° C.

The compound shown below was employed as the comparison substance in the following use examples:

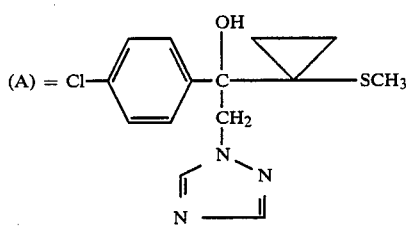

(known from EP-OS (European Published Specification) No. 0,810,136).

EXAMPLE A

*Fusarium Culmorum* Test (Wheat)/Seed Treatment

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the wheat are sown 1 cm deep in standard soil and are cultivated in a greenhouse at a temperature of about 18° C. in seedboxes which are exposed to light for 15 hours daily.

About 3 weeks after sowing, the plants are evaluated for symptoms.

In this test, the compound (I-1) according to the invention shows a distinctly better activity than the comparison substance (A).

EXAMPLE B

Cercospora test (mung bean)/protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Cercospora canescens and then remain in a dark humidity chamber at 22° C. and 100% relative humidity for one day.

The plants are then placed under illumination in a greenhouse at 23° C. and 80% relative humidity.

Evaluation is carried out about 20 days after the inoculation.

In this test, the compound (I-1) according to the invention shows a better activity than the comparison substance (A).

It will be appreciated that the instant specification and claims are set forth by way of illustration and not limitation, and that various modifications and changes may be made without departing from the spirit and scope of the present invention.

We claim:

1. An azolylmethyl-cyclopropyl carbinol derivative of the formula

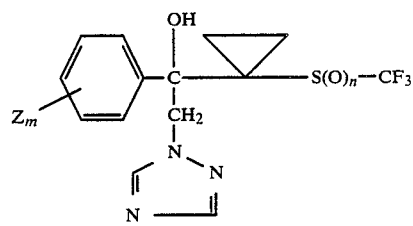

in which
Z is fluorine, chlorine or methyl,
m is 0,1,2 or 3, and
n is 0, 1 or 2, or an addition product thereof with an acid or metal salt.

2. A compound according to claim 1 wherein such compound is 1-(2,4-difluorophenyl)-1-hydroxy-2-(1,2,4-triazol-1-yl)-1-(1-trifluoromethylmer-capto-cycloprop-1-yl)ethane of the formula

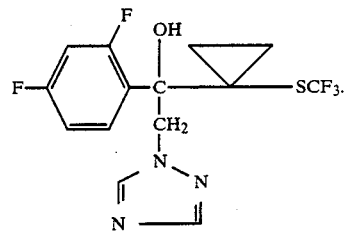

3. A compound according to claim 1 wherein such compound is 1-(2,4-difluorophenyl)-1-hydroxy-2-(1,2,4-triazol-1-yl)-1-(trifluoromethylsulphoxy-cycloprop-1-yl)-ethane of the formula

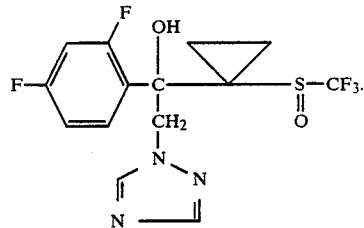

4. A compound according to claim 1 wherein such compound is 1-(4-methylphenyl)-1-hydroxy-2-(1,2,4-triazol-1-yl)-1-(1-trifluoromethylmercapto-cycloprop-1-yl)ethane of the formula

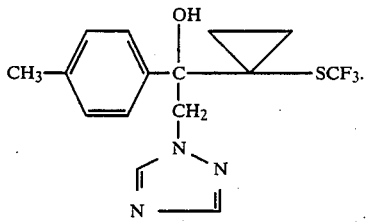

5. A compound according to claim 1 wherein such compound is 1-(4-fluorophenyl)-1-hydroxy-2-(1,2,4-triazol-1-yl)-1-(1-trifluoromethylmercapto-cycloprop-1-yl)ethane of the formula

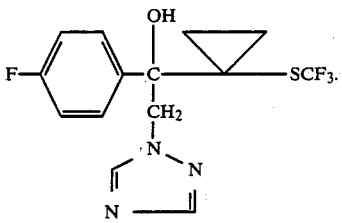

6. A compound according to claim 1 wherein such compound is 1-phenyl- 1-hydroxy-2-(1,2,4-triazol-1-yl)-(1-trifluoromethylmercapto-cycloprop-1-yl)ethane of the formula

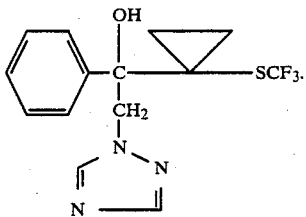

7. A fungicidal composition comprising a fungicidally effective amount of a compound or addition product thereof according to claim 1 and an inert diluent.

8. A method of combating fungi which comprises applying to such fungi or to a fungus habitat a fungicically effective amount of a compound or addition product thereof according to claim 1.

9. The method according to claim 8, wherein such compound is
(2,4-difluorophenyl)-1-hydroxy-2-(1,2,4-triazol-1-yl)-1-(1-trifluoromethylmercapto-cycloprop-1-yl)ethane,
(2,4-difluorophenyl)-1-hydroxy-2-(1,2,4-triazol-1-yl)-1-(trifluoromethylsulphoxy-cycloprop-1-yl)ethane,
(4-methylphenyl)-1-hydroxy-2-(1,2,4-triazol-1-yl)-1-(1-trifluoromethylmercapto-cycloprop-1yl)ethane,
(4-fluorophenyl)-1-hydroxy-2-(1,2,4-triazol-1-yl)-1-(1-trifluoromethylmercapto-cycloprop-1-yl)ethane, or
phenyl-1-hydroxy-2-(1,2,4-triazol-1-yl)-1-(1-trifluoromethylmercapto-cycloprop-1-yl)ethane, or an addition product thereof with an acid or metal salt.

10. A plant-growth regulating composition comprising a plant-growth regulating effective amount of a compound or addition product thereof according to claim 1 and an inert diluent.

11. A method of regulating the growth of plants which comprises applying to such plants or to a locus in which such plants are growing or are to be grown a plant-growth regulating effective amount of a compound or addition product thereof according to claim 1 and an inert diluent.

12. The method according to claim 11, wherein such compound is
10(2,4-difluorophenyl)-1-hydroxy-2-(1,2,4-triazol-1yl)-1-(1-trifluoromethylmercapto-cycloprop--1-yl)ethane,
1-(2,4-difluorophenyl)-1-hydroxy-2-(1,2,4-triazol-1-yl)-1-(trifluoromethylsulphoxy-cycloprop-1yl)-ethane,
1-(4-methylphenyl)-1hydroxy-2-(1,2,4-triazol-1-yl)-1-(1-trifluoromethylmercapto-cycloprop-1-yl)-ethane, or
1-phenyl-1-hydroxy-2-(1,2,4-triazol-1yl)-1(1-trifluoromethylmercapto-cycloprop-1-yl)ethane.

* * * * *

UNITED STATES PATENT AND TRADEMARK OFFICE
CERTIFICATE OF CORRECTION

PATENT NO. : 4,954,162

DATED : September 4, 1990

INVENTOR(S) : Stroech et al.

It is certified that error appears in the above-identified patent and that said Letters Patent is hereby corrected as shown below:

Title Page     [75] Second Inventor delete " Beilefeldt" and substitute -- Bielefeldt --

Col. 21, line 28    After " -1-yl) " insert -- 1- --

Col. 22, line 7    Before " (2,4-difluorophenyl) " insert -- 1- --

Col. 22, line 10    Before " (2,4-difluorophenyl) " insert -- 1- --

Col. 22, line 12    Before " (4-methylphenyl) " insert -- 1- --

Col. 22, line 14    Before " (4-fluorophenyl) " insert -- 1- --

Col. 22, line 17    Before " phenyl " insert -- 1- --

Col. 22, line 33    Delete " 10 " and substitute -- 1- -- and substitute -- 1-y

Col. 22, line 41    After " ethane, " insert -- 1-(4-fluorophenyl)-1-hydroxy-2-(1,2,4-triazol-1-yl)-1-(1-trifluoromethyl-mercapto-cycloprop-1-yl)-ethane, --

Signed and Sealed this

Eleventh Day of August, 1992

Attest:

DOUGLAS B. COMER

*Attesting Officer*     *Acting Commissioner of Patents and Trademarks*